United States Patent [19]

Ikeda et al.

[11] Patent Number: 5,346,469
[45] Date of Patent: Sep. 13, 1994

[54] HANDPIECE FOR SURGICAL OPERATION

[75] Inventors: Tadaaki Ikeda, Yokohama; Morito Idemoto, Akita, both of Japan

[73] Assignee: Sumitomo Bakelite Company Limited, Tokyo, Japan

[21] Appl. No.: 85,771

[22] Filed: Jun. 25, 1993

[30] Foreign Application Priority Data

Oct. 7, 1992 [JP] Japan .................... 4-268859

[51] Int. Cl.⁵ ................ A61B 17/20; A61B 17/32
[52] U.S. Cl. ..................... 604/22; 606/171
[58] Field of Search ........... 604/22; 606/161, 159, 606/167, 169, 170, 171

[56] References Cited

U.S. PATENT DOCUMENTS

| | | | |
|---|---|---|---|
| 4,178,935 | 12/1979 | Gekhman et al. | |
| 4,922,902 | 5/1990 | Wuchinich et al. | |
| 4,989,588 | 2/1991 | Kubota et al. | 128/24 A |
| 5,002,557 | 3/1991 | Hasson | |
| 5,015,227 | 5/1991 | Broadwin et al. | |
| 5,180,363 | 1/1993 | Idemoto et al. | 202/32 |
| 5,188,102 | 2/1993 | Idemoto et al. | 128/24 A |
| 5,205,817 | 4/1993 | Idemoto et al. | 604/22 |
| 5,209,719 | 5/1993 | Baruch et al. | 604/22 |
| 5,242,385 | 9/1993 | Strukel | 604/22 |
| 5,255,669 | 10/1993 | Kubota et al. | 128/24 AA |

FOREIGN PATENT DOCUMENTS

| | | |
|---|---|---|
| 443256 | 12/1990 | European Pat. Off. |
| 482847 | 10/1991 | European Pat. Off. |
| 3707567 | 9/1987 | Fed. Rep. of Germany |
| 4040537 | 8/1991 | Fed. Rep. of Germany |
| 9210139 | 6/1992 | World Int. Prop. O. ........... 604/22 |

Primary Examiner—John D. Yasko
Assistant Examiner—Adam J. Cermak
Attorney, Agent, or Firm—Browdy and Neimark

[57] ABSTRACT

A handpiece for preventing the visual field of an endoscope from being disturbed by irrigation liquid, and which performs safely and reliably selective separation of biological tissue such as a blood vessel or the like by ultrasonic vibration, in operation under a visual field of an endoscope which is restricted in operation has a tip section of 5/4 or 7/4 times wavelength, a forward end curved in an arcuate form, and a tip cover provided with a detachable tip top cover at a forward end, which is semi-transparent or transparent, and which has an inclined surface, to prevent irrigation liquid from scattering. The tip cover of an ultrasonic surgical knife is provided with an auxiliary cavity for a laser probe, and a spatula-like projection at the forward end of the cover. The main cavity and the auxiliary cavity for the tip are closed by an O-ring gas-tight packing or a gas-tight closure to prevent pneumoperitoneum gas within an abdomen cavity from leaking.

13 Claims, 7 Drawing Sheets

HANDPIECE FOR SURGICAL OPERATION

BACKGROUND OF THE INVENTION

The present invention relates to a handpiece for surgical operation for crushing and removing foreign bodies within a biological histology or within a coeloma or a body cavity by ultrasonic vibration or oscillation.

As a surgical operating device for crushing or cutting and separating or amputating a biological histology by ultrasonic vibration, a surgical operating device is known whose object is soft histology or tissue for ophthalmology in which lenses hardened by a cataract are crushed, drawn or evacuated and removed, and one is known for general surgery in which a tumor and a hematoma generated in brain, spine, digestive organ and the like are crushed, drawn and removed. Further, in recent years, an ultrasonic operating device has been utilized which can cut and separate or isolate hard histology by ultrasonic vibration.

Furthermore, among various kinds of manipulations and devices developed for performing medical treatment by minimal invasion and non-invasion, an operation for extracting a gallbladder by the use of a laparoscope is now in wide use, particularly for digestive organ surgery because recovery is fast and hospital stays are short so that rehabilitation can also be fast, pain after operation is reduced, the operative wound created in the surgery is extremely small and the like, since there is less in operational invasion as compared with ventrotomy operation.

The operation is such that a pneumoperitoneum is made to the interior of the peritoneal cavity by carbonic acid gas or the like without ventrotomy, and a trocar is used to insert an endoscope, forceps, an electrocautery or the like into the interior of the peritoneal cavity, and the gallbladder is extracted under the field of vision of the endoscope. A point thereof is that a cystic duct and a cystic artery are peeled off or ablated safely and accurately from a Calot's triangle, clipping is made to the cystic duct and the cystic artery to cut the latter, and a cystic fundus is ablated from a liver bed section to grasp or grip the gallbladder by the forceps, to thereby remove the cystic fundus out of the body.

Moreover, there are caused the following problems and the like. That is, if an attempt is made to apply the operation under the endoscope to all cases of cholelithiasis, the use of ordinary grasper causes macroapoplexy from artery and the liver bed section, and makes it difficult to fix the cystic duct and the cystic artery, and the like, depending upon conditions such as inflammatory degree of the gallbladder, a position of gallstone, configuration of the cystic duct, the cystic artery and the like, age of a patient and the like. There is a danger that switching must be made to ventrotomy operation during the operation. On the contrary, counterplan or countermeasures are taken such as an improvement in hemostatic effects due to an improvement of configuration of a forward end of the electrocautery, hemostasis by the use of a laser surgical knife, or the like. However, since a mechanical tearing force of forceps is used for the visual field disturbance due to smoke and for peeling or separation of the cystic duct and the cystic artery, this is not basic bleeding prevention.

In view of the above, trials are made such that a surgical operating device due to ultrasonic vibration, capable of selectively preserving or retaining a resilient or elastic body such as blood vessels or the like is used to carry out these operations.

However, there are fears that, since the operation is one under reduced or narrow visual field of the endoscope, it is impossible to pass the handpiece from one hand to the other to change the inserting position dissimilarly to the ventrotomy operation, and irrigation liquid jetted from a tip section at a forward end of a handpiece is applied to lenses, since a distance between an objective lens of the endoscope and a portion to be operated is short such as few cm.

For example, as shown in FIGS. 11A and 11B, in a case where a cystic duct 36 connected to a gallbladder 37 is peeled off or separated, an inserting direction of a tip 100 at a forward end of a handpiece is limited or restricted by a direction of a trocar which pierces into a laparotomy from the outside of the body. Accordingly, it is difficult to separate a fundus of the cystic duct 36. Moreover, under a condition illustrated in FIGS. 12A and 12B, irrigation liquid jetted from a clearance or gap between a tip cover 101 and a tip 100 by vibration of the tip 100 scatters over a wide range, resulting in clouding of the lenses of the endoscope.

Further, in a case of the operation under the endoscope, a vibrator section such as a tip or the like which is inserted into the body is lengthened. For this reason, it is difficult to judge as to whether or not the irrigation liquid is surely or reliably supplied up to the forward end of the tip. In a case where the tip is vibrated under a condition that the irrigation liquid is insufficient, there is a fear that the irrigation liquid of high temperature is jetted so that tissues are damaged. Thus, countermeasures are required.

SUMMARY OF THE INVENTION

The invention has an object thereof to solve the above-discussed problems of the conventional handpiece for surgical operation in which ultrasonic vibration is used, and has an object thereof to provide a handpiece for surgical operation which prevents visual field disturbance of an endoscope from occurring due to jetting of irrigation liquid in operation under narrow visual field of the endoscope, which can perform safely 1 and correctly separation of a blood vessel or the like and which can use also a laser probe.

According to the invention, there is provided a handpiece for surgical operation for crushing or cutting and separating to remove a biological histology or foreign bodies within a body cavity by ultrasonic vibration, characterized by comprising a source of ultrasonic vibration, a vibrator having a joint section and a tip section reduced in diameter, the vibrator being connected to the source of ultrasonic vibration for transmitting and enlarging mechanical vibration of ultrasonic frequency, and a cover made of heat-resistant resin for receiving and covering the source of ultrasonic vibration and the vibrator, wherein the source of ultrasonic vibration and the vibrator communicate with each other and are connected to each other by a suction passage which passes through the source of ultrasonic vibration, the vibrator and the cover in a lengthwise direction, wherein the cover has, in combination, a body cover for receiving the source of ultrasonic vibration and the joint section of the vibrator and a tip cover for covering the tip section, and wherein the vibrator has a forward end thereof of the tip section which is curved in arcuate configuration.

Furthermore, the tip section of the vibrator is such that an entire length from a rearward end joining to the joint section to a working portion at a forward end has a value corresponding to substantially 5/4 times or 7/4 times the wavelength, that a curvature point of the forward end of the tip section is located at a position equal to or more than 3/100 wavelength from the forward end of the tip section and within 30 mm, that a curvature angle thereof is equal to or smaller than 35°, that the forward end of the tip cover is one on which a tip top cover is mounted which is so formed as to be detachable, and which is semi-transparent or transparent, and that a forward end surface of the tip cover (the forward end surface at the time the tip top cover is mounted) has an angle with respect to an axis of the vibrator in a lengthwise direction.

Moreover, there is provided a handpiece for surgical operation, characterized in that the tip cover has a main cavity through which the tip section is inserted, and an auxiliary cavity provided in parallel relation to the main cavity within a side wall of the tip cover, a gas tight packing being additionally provided on a proximal portion of the tip cover. Furthermore, there is provided a handpiece for surgical operation, characterized in that the forward end of the tip portion of the vibrator is curved in arcuate configuration, that the tip cover has an O-ring on an inner surface of the main cavity in the proximal end of the tip cover, the O-ring being mounted in intimate or close contact relation to an outer periphery of the vibrator at a position which is brought to a node of the ultrasonic vibration of the vibrator, and that the forward end of the tip cover is brought to an inclined or tilting surface in a direction which connects a center of the main cavity and a center of the auxiliary cavity to each other, the tip cover having a spatula-like projection at a pointed end of the inclined surface, and that the tip cover is mounted rotatably about an axis that is the tip section of the vibrator which is inserted into the main cavity.

DESCRIPTION OF THE EMBODIMENTS

The invention will hereunder be described in detail with reference to the accompanying drawings.

Figure 1A:
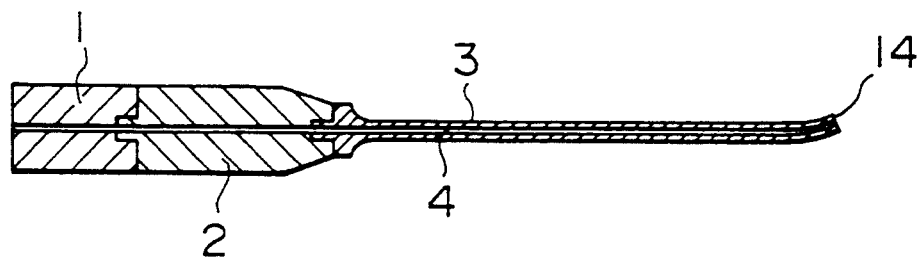
FIGS. 1A, 1B, 1C and 1D are cross-sectional views showing a fundamental or basic structure of a handpiece for surgical operation which forms an embodiment of the invention.
Figure 1B:
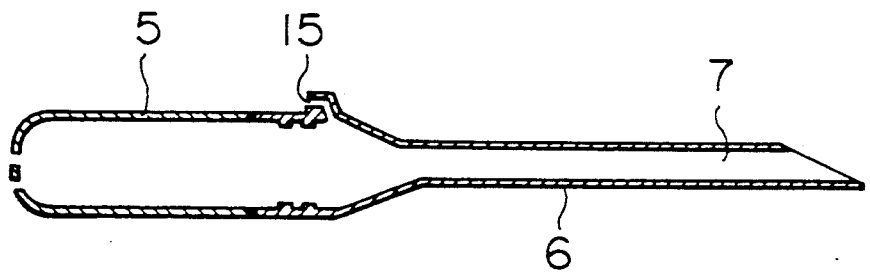
Figure 1C:
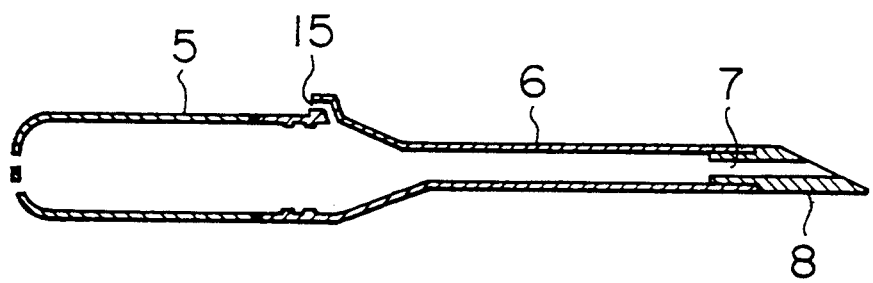
Figure 1D:
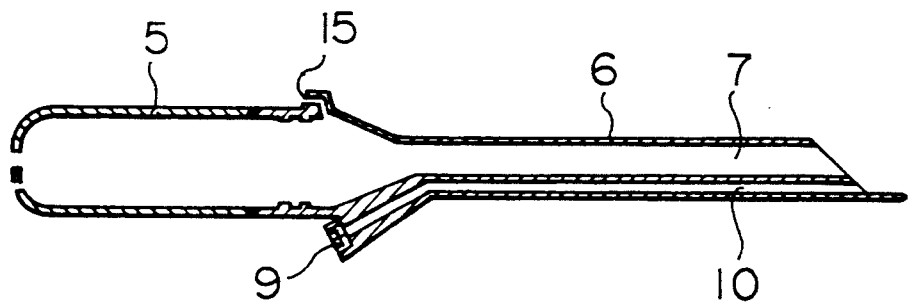
Figure 2A:
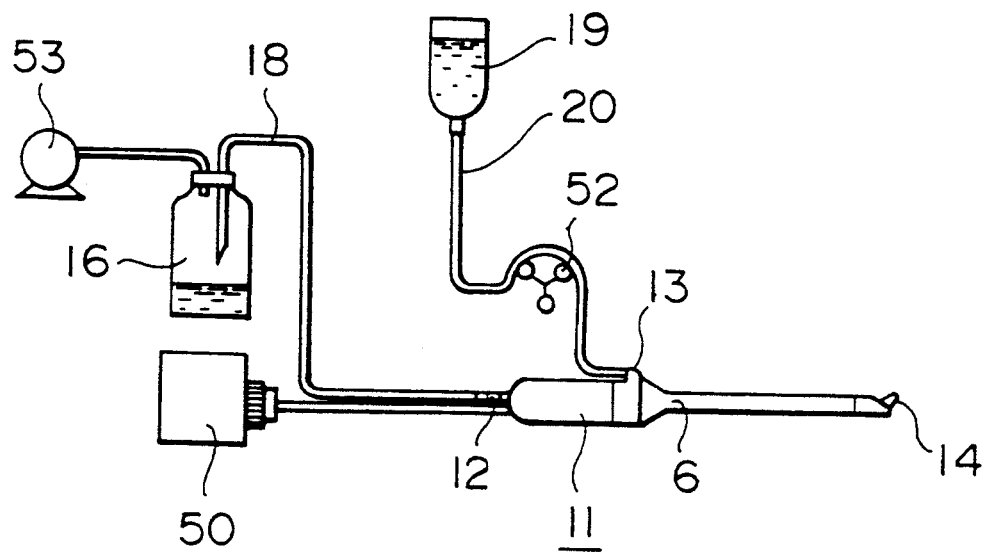
FIGS. 2A and 2B are views showing an entire system which utilizes the handpiece for surgical operation according to the invention.
Figure 2B:
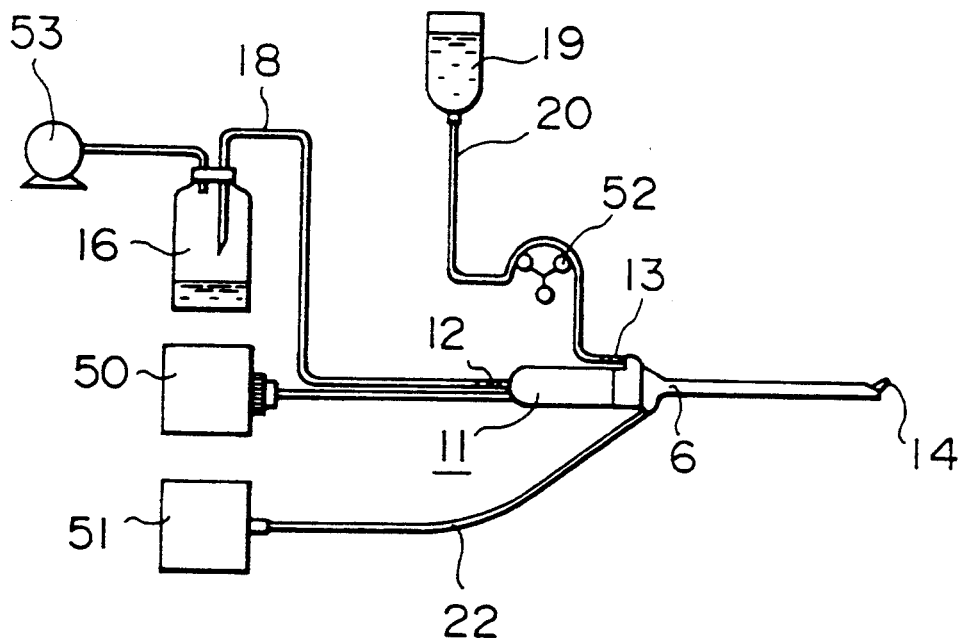

FIGS. 1A, 1B, 1C and 1D are cross-sectional views for explanation of a basic structure of a handpiece for surgical operation, according to an embodiment of the invention, while FIGS. 2A and 2B are views showing an entire system which utilizes the handpiece for surgical operation, according to the invention.

A source of ultrasonic vibration 1 is joined to a vibrator having a joint section (2) and a tip section 3, by means of screws or the like as shown in FIG. 1A. The joint section 2 and the tip section 3 are provided therein with a suction passage 4 which passes through the joint section 2 and the tip section 3 in a lengthwise direction. The joint section 2 and the tip section 3 are manufactured separately from each other as shown in FIGS. 1A to 1D and 2A and 2B, and may be joined to each other by means of screws or the like. However, there is no hindrance if the joint section 2 and the tip section 3 are formed integrally.

On the other hand, as shown in FIGS. 1B, a cover made of heat-resistant resin for receiving and covering the above-described elements which are vibrated ultrasonically is arranged by combination of a body cover 5 for receiving the source of ultrasonic vibration 1 and the joint portion 2, and a tip cover 6 for covering a forward end of the joint portion 2 and the tip portion 3. The body cover 5 has a rearward end thereof which is provided therein with an opening at which a suction nipple 12 is additionally provided on a rearward end of the suction passage 4, and an opening for a cable for supplying high-frequency electric power to the source of ultrasonic vibration 1 from an ultrasonic oscillator 50. Further, the tip cover 6 has an inner cavity 7 through which the tip portion 3 is inserted. When the tip portion 3 is inserted into the inner cavity 7, an annular space generated between the inner cavity 7 and the tip portion 3 is utilized as a passage for supplying irrigation liquid such as physiological saline solution or the like. However, the tip cover 6 has a proximal end thereof which is provided with an irrigation bore 15 which serves as an inlet for irrigation liquid.

A using method of the handpiece 11 for surgical operation according to the invention is as follows: First, as shown in FIGS. 2A and 2B, the high frequency electric power of resonant frequency is supplied to the source for ultrasonic vibration 1 within the handpiece 11, from the ultrasonic oscillator 50, to generate ultrasonic vibration thereat. The ultrasonic vibration is transmitted and enlarged by the vibrator in which the joint section 2 and the tip section 3 are combined with each other. At a working portion 14 at the forward end of the tip section, crushing or fragmentation operation of biological histology or the like is performed. Simultaneously with start of the vibration, a roller pump 52 operates so that the irrigation liquid is injected into the tip cover 6 from a bottle 19 through an irrigation tube 20 and an irrigation nipple 13. The irrigation liquid passes through an annular passage between the inner wall of the inner cavity 7 and the tip section 3, and is jetted toward the working portion 14 from the forward end of the tip cover, by the ultrasonic vibration. The biological histology or the like is crushed or fragmented and emulsified by the ultrasonic vibration of the irrigation liquid and the working portion 14. Emulsified crushed pieces pass through the suction nipple 12 and a suction tube 18 through the tip section 3, the joint section 2 and the suction passage 4 within the source of ultrasonic vibration 1, by suction pressure of a suction pump 53, and are collected at a suction bottle 16. Furthermore, smoke which is generated within an abdomen cavity when the laser surgical knife and electricity are used together can be exhausted to the outside of the body through the suction passage 4 within the handpiece. Accordingly, it is possible to reduce or lighten the visual field disturbance due to the smoke.

The tip cover 6 may include a tip top cover 8 which is mounted thereon as a separate demontable part and formed of a semi-transparent or transparent material, as shown in FIG. C. By doing so, since the tip top cover 8 is semi-transparent or transparent, it is possible for an operator who looks or sees an endoscope image to confirm or affirm, by himself, the supply state of affairs or supply circumstances of the irrigation liquid into the tip top cover 8. Thus, there can be provided an advantage that it is possible to prevent tissues from being damaged resulting from a rise in temperature due to a shortage or insufficiency of the irrigation liquid. It is needless to say that the whole tip cover 6 may be formed by a semi-transparent or transparent material. However, under the present condition that it is difficult to obtain an object or article having sufficient heat resistance by semi-transparent or transparent resin, a method is useful in which the tip top cover 8 shown in FIG. 1C is used together. Further, since the tip top cover 8 is connected to the tip cover 6 by screws or the like and is detachable thereto, there is also provided an advantage that tip top covers 8 different in opening dimension or size from each other can be replaced in accordance with an operational manner.

Figure 4A:
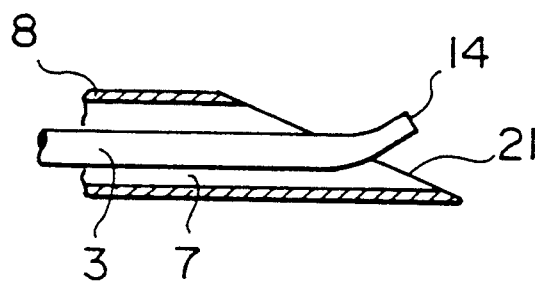
FIGS. 4A and 4B are cross-sectional views showing configuration of a forward end of a tip top cover.
Figure 4B:
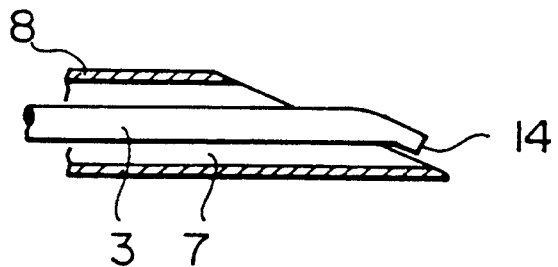
Figure 9A:
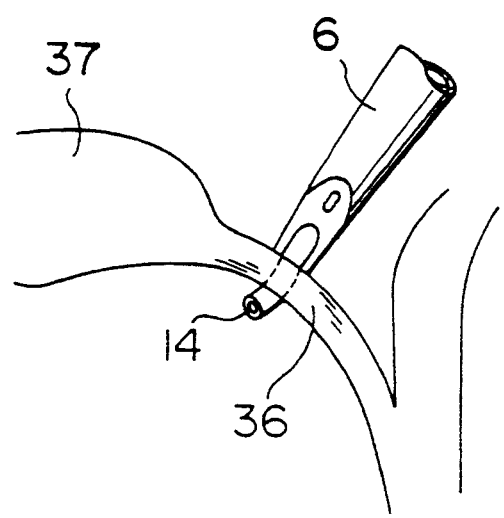
FIGS. 9A and 9B are views showing a using example of the handpiece for surgical operation, according to the invention.
Figure 9B:
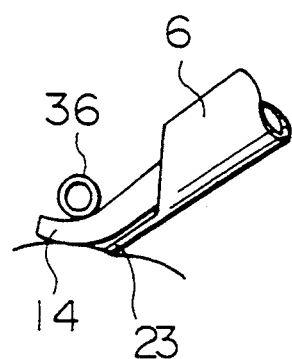
Figure 10A:
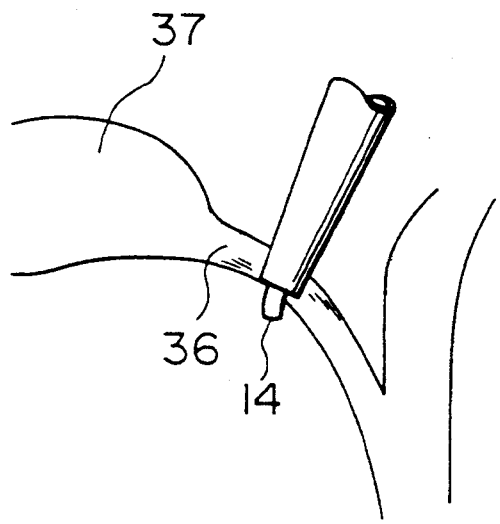
FIGS. 10A and 10B are views showing a using example of the handpiece for surgical operation, according to the invention.
Figure 10B:
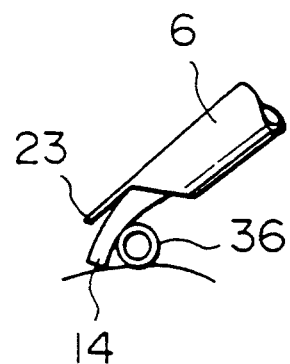
Figure 11A:
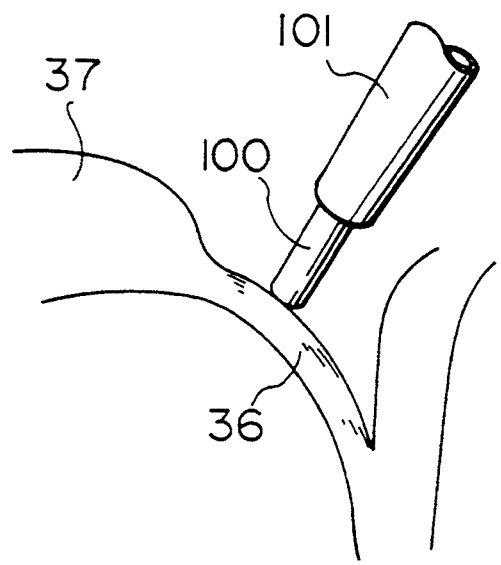
FIGS. 11A and 11B are views showing a using example of a conventional handpiece for surgical operation.
Figure 11B:
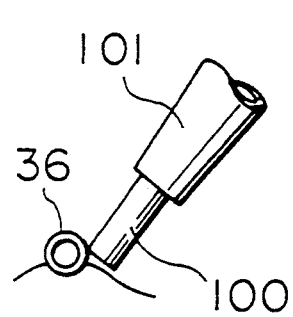
Figure 12A:
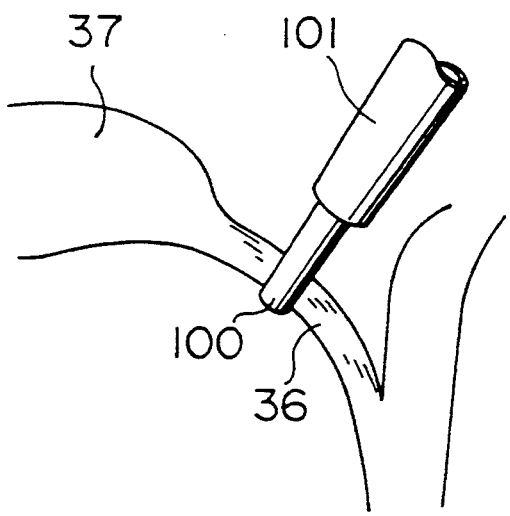
FIGS. 12A and 12B are views showing a using example of a conventional handpiece for surgical operation.
Figure 12B:
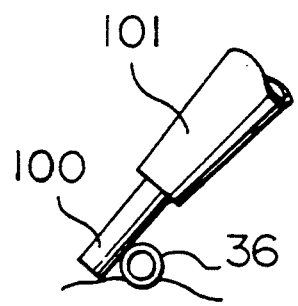

Moreover, it is preferable that the forward end of the tip cover 6 or the tip top cover 8 is brought to an inclined surface having an angle of 10–80 degrees with respect to the axis in the lengthwise direction and, more preferably, 45–60 degrees. By doing so, there can be provided the following advantages. That is, the jetting direction of the irrigation liquid due to the ultrasonic vibration at the working portion 14 of the tip forward end is limited or restricted. It is possible to prevent the irrigation liquid from scattering and being adhered or bonded to the endoscope lenses. Furthermore, as shown in FIGS. 4A and 4B, an inclined section 21 is provided, and the tip top cover 8 can be rotated about the lengthwise axis of the vibrator. By doing so, it is made possible to vary a surface area of the working portion 14 at the forward end of the tip section which is exposed from the forward end of the tip cover. Thus, it is possible to identify blood vessels or the like by the ultrasonic vibration while the blood vessels and the biological histology are floated as shown in FIGS. 9A and 9B, and while the blood vessels and the biological histology are held down or pressed down and retained as shown in FIGS. 10A and 10B.

The handpiece for surgical operation, according to the invention, is used such that the handpiece is inserted into the peritoneal cavity together with the endoscope or the like, through the trocar which is arranged through the abdomen wall. Normally, 220–270mm is required as the length of the tip section 3 having a reduced or fine diameter. Further, the jointing portion between the joint section 2 and the tip section 3 is required to be provided in the vicinity of a node surface of the ultrasonic vibration in consideration of a problem such as fatigue and breakage of a material due to vibration. On the other hand, the working portion 14 at the forward end of the tip section is brought to an antinode surface of the vibration in view of the necessity that an amplitude is maximized. The wavelength of the ultrasonic vibration is determined or decided depending upon frequency of vibration, a material (density) of the vibrator, dimension or size of an outer diameter of the vibrator, and the like. As an example, for the tip section having an outer diameter of 4 mm made of stainless steel, the wavelength at the time frequency is 24 KHz is about 211 mm, and at 38 KHz, the wavelength is about 133 mm. Synthesizing these conditions, it is adequate that the length of the tip section of the handpiece is brought to a length corresponding to substantially 5/4 times the wavelength or 7/4 times the same.

Figure 3:
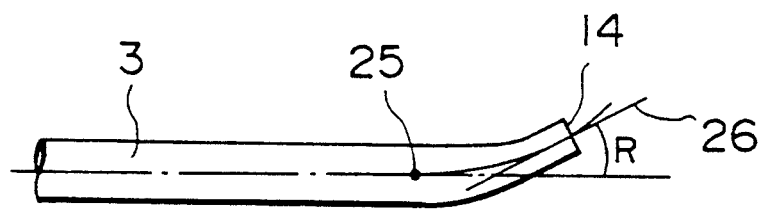
FIG. 3 is a view for explanation of configuration of a forward end of a tip section in the invention.

Furthermore, in order to increase the amplitude in the lengthwise axial direction in the working portion 14, it is effective that the neighborhood of the forward end of the tip section 3 is reduced in thickness and is curved. As shown in FIG. 3, a curvature point 25 from which the forward end starts to be curved from the lengthwise axis is a position spaced equal to or more than 3/100 wavelength away from the forward end of the tip section. However, in consideration of the relationship with respect to the tip cover, the curvature point 25 is within 30 mm. Moreover, it is required that a curvature angle R which is formed by a tangent 26 with respect to the longitudinal or lengthwise axis at the forward end of the curved tip portion is equal to or less than 35 degrees. If the curvature angle R is equal to or more than 35 degrees, the effects with respect to the amplitude are reduced, and this is not preferable also from the point of view of operability of the working portion 14.

Next, it is preferable that the opening of the suction passage at the forward end of the working portion 14 is smaller than the diameter of the suction passage 4 within the tip portion 3. By doing so, there can be produced an advantage that it is possible to prevent objects to be sucked or drawn from being packed or jammed at the node portion of the vibration of the tip portion 3 to block the passage.

Figure 5A:
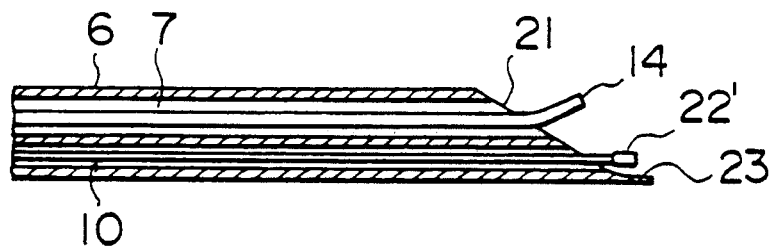
FIGS. 5A and 5B are cross-sectional views showing a condition under which the tip section and a laser probe are inserted into the tip cover.
Figure 5B:
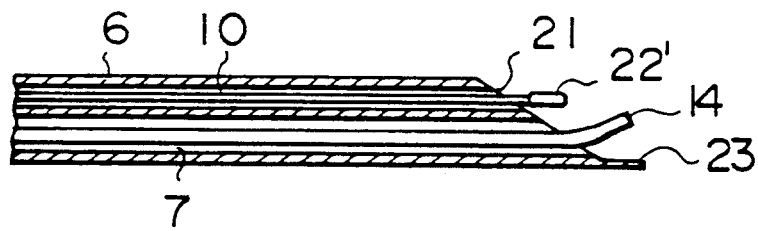

Moreover, as shown in FIG. 1D, an auxiliary cavity 10 is provided within the side wall of the tip cover in parallel to the main cavity 7 through which the tip section 3 of the tip cover 6 is inserted, whereby an applied scope or range of the handpiece according to the invention is further widened. The proximal end of the auxiliary cavity 10 is additionally provided with a gas-tight packing 9 for holding or retaining gas tightness at the time a tube, a wire or the like is inserted into the auxiliary cavity 10. Use is made to insert a probe such as a laser surgical knife, an electro surgical knife and the like into the auxiliary cavity 10 in the tip cover 6, as occasion demands. In an example illustrated in FIG. 2B, use is made such that a laser probe 22 connected to a laser oscillator 51 is inserted into the auxiliary cavity 10 through the gas-tight packing 9 provided at the proximal end of the tip cover 6, and a laser probe working portion 22' projects from an inclined portion 21 at the forward end of the tip cover, as shown in FIGS. 5A and 5B. The laser probe 22 used is not particularly limited to a specific one if the laser probe 22 is superior in flexibility.

It is preferable that, as shown in FIGS. 5A and 5B, the forward end of the tip cover 6 is made to have the inclined surface included in a direction connecting a center of the main cavity 7 and a center of the auxiliary cavity 10 to each other, and a spatula-like projection 23 is provided at a pointed end of the inclined surface. Orientation of the inclination of the inclined portion 21 may be either of those illustrated in FIGS. 5A and 5B. In an example illustrated in FIG. 5A, there is provided an advantage that when solidifying working is done at the laser probe working portion 22',it is possible to prevent heat or thermal damage from being applied to surrounding other tissues by the spatula-like projection 23. Further, in an example illustrated in FIG. 5B, there is provided an advantage that the jetting direction of the irrigation liquid due to the ultrasonic vibration of the tip working portion 14 can be limited or restricted, and it can be prevented that the irrigation liquid is scattered to adhere to the endoscope lenses. Moreover, by the fact that the inclined portion 21 and the spatula-like projection 23 are provided, it is possible to fix the blood vessels and the like by the ultrasonic vibration and to perform hemostasis due to the laser probe 22 while the blood vessels, the biological histology and the like are retained in floating and in holding down. Furthermore, since smoke generated at hemostasis due to the laser can be exhausted to the outside of body by the suction passage 4 within the handpiece, it is possible to prevent the visual field from being disturbed by the smoke.

Figures 7A, 7B, 7C:
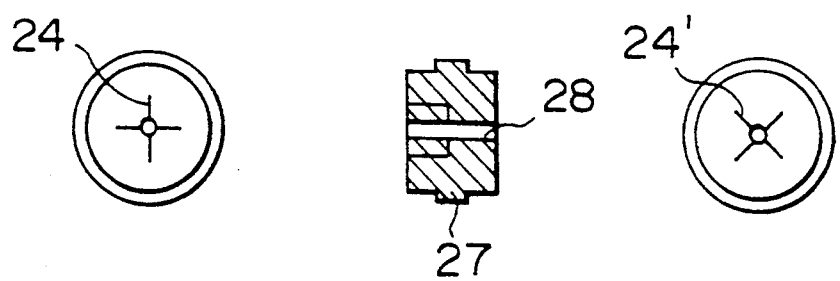
FIG. 7A is a rear elevational view showing a structure of a gas-tight packing.
FIG. 7B is a side elevational cross-sectional view showing the structure of the gas-tight packing.
FIG. 7C is a front elevational view showing the structure of the gas-tight packing.

The gas-tight packing 9 at the proximal end of the auxiliary cavity 10 into which the laser probe 22 is inserted has a role to prevent the pneumoperitoneum gas from leaking. The gas-tight packing 9 is made of a rubber-like elastic material. As shown in FIGS. 7A, 7B and 7C, the gas-tight packing 9 has an inserting bore 28 for the laser probe at a center of the gas-tight packing 9. The gas-tight packing 9 has a rearward end surface and a front end surface thereof which are provided respectively with cuts 24 and 24' so as to be intersected to each other at an angle of 45°. Even after the laser probe or the like has repeatedly been inserted and demounted, the arrangement is such that gas tightness upon the use can be held or retained. Moreover, mounting of the auxiliary cavity 10 on the proximal end can easily be fixed by fitting of a holding projection 27.

Figure 8A:
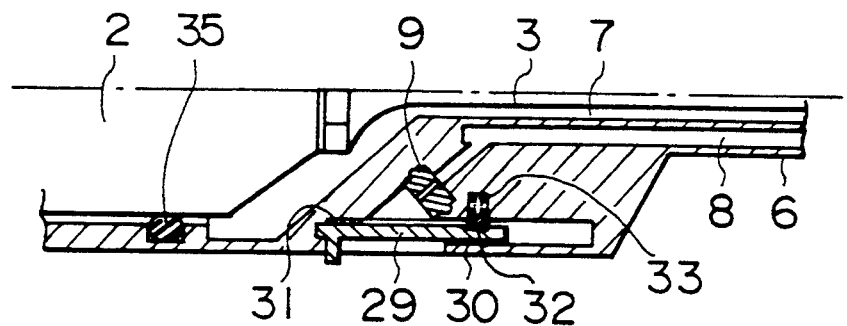
FIGS. 8A and 8B are fragmentary cross-sectional views showing a structure of a proximal end of an auxiliary cavity in the tip cover.
Figure 8B:
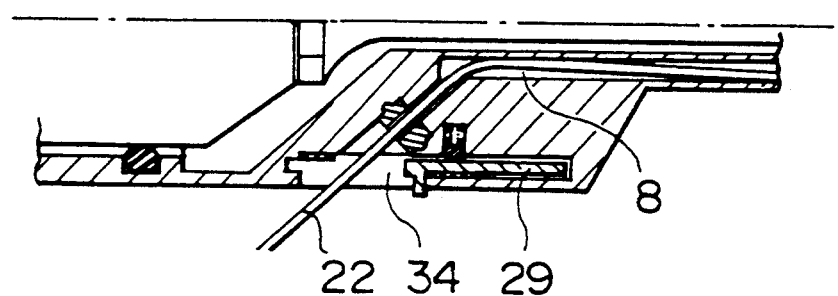

Furthermore, for the purpose of retention of gas tightness at the time the laser probe or the like is not inserted and used, a gas-tight closure 29 is provided at the proximal end of the auxiliary cavity 10 as shown in FIGS. 8A and 8B. The gas-tight closure 29 is pressed down by packings 31 and 30 and a ball 32 and a spring 33 under a closed condition (FIG. 8A) so as to be capable of retaining gas tightness. Under a condition (FIG. 8B) in which the gas-tight closure 29 is open, it is possible to insert the laser probe 22 or the like through a probe inserting opening 34. Under this condition, gas tightness can be retained by the gas-tight packing 9. In this manner, it is possible to prevent the pneumoperitoneum gas from leaking, and it is possible to prevent visual field from being reduced and gas from losing by gas leakage.

Figure 6:
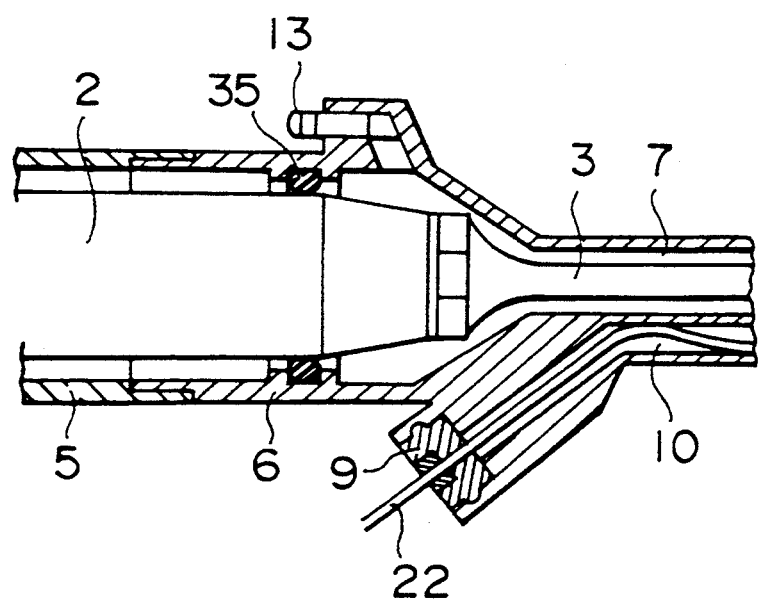
FIG. 6 is an enlarged cross-sectional view showing a structure in the vicinity of a proximal end of the tip cover.

Next, as shown in FIG. 6, the proximal end of the main cavity 7 in the tip cover 6 is such that an O-ring 35 is arranged on an inner surface of the main cavity 7, and the O-ring 35 is in close or intimate contact with a position which is brought to node of the ultrasonic vibration of the joint section 2 to prevent the irrigation liquid from leaking and to prevent gas from leaking from locations except for or other than the irrigation nipple 13 under a condition that the irrigation liquid is not supplied. Moreover, rearwardly of the irrigation nipple 13, gas tightness is maintained or kept by a rotor of the roller pump 21 in the irrigation tube 20 to prevent pneumoperitoneum gas within the abdomen cavity from leaking from the main cavity 7.

In connection with the above, FIGS. 9A and 9B and 10A and 10B are views showing using examples of the handpiece for surgical operation, according to the invention. FIGS. 9A and 9B show a condition in which a lower portion of a cystic duct 36 connected to a gallbladder 37 is peeled off or separated by the working portion 14 at the forward end of the arcuate tip section, while FIGS. 10A and 10B show a condition in which the handpiece is passed from one hand to the other at the opposite side of the cystic duct 36 to rotate the tip section 3, to thereby change orientation of the working portion 14 without the handpiece being once pulled out and reinserted from another piercing bore without the inserting portion changed, whereby peeling or separation working is made possible, and it is possible to prevent the irrigation liquid from scattering to the endoscope lenses by the inclined portion 21 and the spatula-like projection 23.

Further, it is desired that the tip cover 6 is so formed as to be rotated about the axis of the vibrator in the lengthwise direction at junction or a connecting portion of the body cover 5, to perform positioning and fixing. By doing so, it is made possible that the tip cover 6 is rotated in accordance with the state of affair or circumstances of an operating portion during operation to change orientation of the surface of the inclined portion 21 at the forward end to adjust the jetting direction of the irrigation liquid. Thus, it is possible that affection or influence to the visual field of the endoscope due to scattering of the irrigation liquid is avoided to proceed operation more smoothly.

According to the invention, there are provided the following advantages. That is, in an operation under the endoscope by the handpiece for surgical operation, which utilizes the ultrasonic vibration, it is possible to accurately and safely perform identification for blood vessels or the like, it is possible to perform hemostasis by the use of the laser surgical knife or the like upon bleeding, and it is possible also to prevent the endoscope lenses from clouding due to scattering of the irrigation liquid. Not only it is possible to perform operation smoothly, but also an attempt is made to enlarge applied cases. Thus, the handpiece for surgical operation, according to the invention, is useful as a handpiece for surgical operation.

What is claimed is:

1. A handpiece for surgical operation, for crushing, or cutting, separating and removing foreign bodies within biological histology or a body cavity by ultrasonic vibration, comprising:
   a source of ultrasonic vibration;
   a vibrator having a joint section and a tip section reduced in diameter, connected to the source of ultrasonic vibration for transmitting and enlarging mechanical vibration of ultrasonic frequency, and a cover made of heat-resistant resin for receiving and covering said source of ultrasonic vibration and said vibrator, wherein the source of ultrasonic vibration and the vibrator communicate with each other and are connected to each other by a suction passage extending therethrough in a lengthwise direction, wherein said cover has, in combination, a body cover for receiving therein said source of ultrasonic vibration and the joint section of said vibrator and a tip cover for covering said tip section, and wherein said tip section of said vibrator has a forward end thereof which is curved in arcuate configuration;

wherein a curvature point of the forward end of the tip section of the vibrator is located within 30 mm and at least 3/100 wavelength from the forward end of the tip section, and wherein a curvature angle is equal to or less than 35 degrees;

wherein said tip cover is so formed as to be rotatable about a longitudinal axis of the vibrator and to be capable of being fixed in a selected position of rotation; and wherein said tip cover has a forward end surface thereof which has an angle with respect to an axis of the vibrator in the lengthwise direction.

2. A handpiece for surgical operation, according to claim 1, wherein said tip section of the vibrator has a node surface of the ultrasonic vibration in the vicinity of a rearward end of said tip section which is coupled to said joint section, and an antinode surface at a working portion at the forward end of said tip section, wherein an entire length from a connecting end to said joint section, to the working portion at the forward end has a value corresponding to one of substantially 5/4 times the wavelength and substantially 7/4 times thereof.

3. A handpiece for surgical operation, according to claim 2, wherein said suction passage within a tip of the vibrator is larger than a diameter of an opening in the suction passage within the forward end of the tip section.

4. A handpiece for surgical operation, according to claim 2, wherein a semi-transparent or transparent tip top cover so formed as to be detachable is mounted on a forward end of the tip cover.

5. A handpiece for surgical operation, according to claim 1, wherein said suction passage within a tip of the vibrator is larger than a diameter of an opening in the suction passage within the forward end of the tip section.

6. A handpiece for surgical operation, according to claim 1, wherein the cover has a cavity formed therethrough comprising a main cavity through which said tip section is inserted and an auxiliary cavity provided within a side wall of the tip cover in parallel relation to said main cavity.

7. A handpiece for surgical operation, according to claim 6, wherein said tip cover has an O-ring on an inner surface of the main cavity in a proximal end of the tip cover, and wherein said O-ring is mounted in intimate contact with an outer periphery of said vibrator at a position which is brought to a node of the ultrasonic vibration of said vibrator.

8. A handpiece for surgical operation, according to claim 7, wherein the forward end of the tip cover is formed with an inclined surface in a direction connecting a center of the main cavity and a center of the auxiliary cavity to each other, wherein the handpiece has a spatula-like projection at a pointed end of said inclined surface, and wherein said tip cover is so mounted as to be rotatable with a tip portion of the vibrator inserted into said main cavity serving as an axis.

9. A handpiece for surgical operation, according to claim 6, wherein a gas-tight packing is additionally provided on a proximal end of an auxiliary cavity which is provided within a side wall of the tip cover.

10. A handpiece for surgical operation, according to claim 9, wherein the forward end of the tip cover is formed with an inclined surface in a direction connecting a center of the main cavity and a center of the auxiliary cavity to each other, wherein the handpiece has a spatula-like projection at a pointed end of said inclined surface, and wherein said tip cover is so mounted as to be rotatable with a tip portion of the vibrator inserted into said main cavity serving as an axis.

11. A handpiece for surgical operation, according to claims 6, wherein the forward end of the tip cover is formed with an inclined surface in a direction connecting a center of the main cavity and a center of the auxiliary cavity to each other, wherein the handpiece has a spatula-like projection at a pointed end of said inclined surface, and wherein said tip cover is so mounted as to be rotatable with a tip portion of the vibrator inserted into said main cavity serving as an axis.

12. A handpiece for surgical operation, for crushing, or cutting, separating and removing foreign bodies within biological histology or a body cavity by ultrasonic vibration, comprising:

a source of ultrasonic vibration;

a vibrator having point section and a tip section reduced in diameter, connected to the source of ultrasonic vibration for transmitting and enlarging mechanical vibration of ultrasonic frequency, and a cover made of heat-resistant resin for receiving and covering said source of ultrasonic vibration and said vibrator, wherein the source of ultrasonic vibration and the vibrator communicate with each other and are connected to each other by a suction passage extending therethrough in a lengthwise direction, wherein said cover has, in combination, a body cover for receiving therein said source of ultrasonic vibration and the joint section of said vibrator and a tip cover for covering said tip section, and wherein said tip section of said vibrator has a forward end thereof which is curved in arcuate configuration;.

wherein a semi-transparent or transparent tip top cover so formed as to be detachable is mounted on a forward end of the tip cover.

13. A handpiece for surgical operation, according to claim 12, wherein a curvature point of the forward end of the tip section of the vibrator is located within 30 mm and equal to or more than 3/100 wavelength from the forward end of the tip section, and wherein a curvature angle is equal to or less than 35 degrees.

* * * * *